United States Patent
Sijbers et al.

(10) Patent No.: US 10,006,907 B2
(45) Date of Patent: Jun. 26, 2018

(54) CARTRIDGE FOR ASSAYS WITH MAGNETIC PARTICLES

(71) Applicant: KONINKLIJKE PHILIPS N.V., Eindhoven (NL)

(72) Inventors: Mara Johanna Jacoba Sijbers, Helden (NL); Petrus Johannes Wilhelmus Van Lankvelt, Boekel (NL); Femke Karina De Theije, Berghem (NL); Jeroen Hans Nieuwenhuis, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 56 days.

(21) Appl. No.: 15/184,280

(22) Filed: Jun. 16, 2016

(65) Prior Publication Data
US 2016/0291004 A1    Oct. 6, 2016

Related U.S. Application Data

(63) Continuation of application No. 12/922,887, filed as application No. PCT/IB2009/051021 on Mar. 11, 2009, now abandoned.

(30) Foreign Application Priority Data

Mar. 17, 2008 (EP) .................................. 08102671

(51) Int. Cl.
*G01N 25/08*  (2006.01)
*G01N 33/543*  (2006.01)
(Continued)

(52) U.S. Cl.
CPC ....... *G01N 33/54333* (2013.01); *B03C 1/282* (2013.01); *B03C 1/288* (2013.01);
(Continued)

(58) Field of Classification Search
None
See application file for complete search history.

(56) References Cited

U.S. PATENT DOCUMENTS 5,981,297 A   11/1999   Baselt
6,300,138 B1  10/2001   Gleason
(Continued)

FOREIGN PATENT DOCUMENTS

CN    101021530 A    8/2007
JP    2006184250     7/2006
(Continued)

OTHER PUBLICATIONS

Megens et al "Magnetic Biochips: A New Option for Sensitive Diagnostics" Journal of Magnetism and Magnetic Materials, vol. 293, 2005, pp. 702-708.
(Continued)

*Primary Examiner* — Xiaoyun R Xu

(57) ABSTRACT

A cartridge for detection of target components in a liquid sample includes a sample chamber, at least two reservoirs that can be furnished with magnetic particles, and at least two corresponding sensitive zones in which solved magnetic particles and/or target components can be detected. When a magnetic actuation field of a given configuration is established in the sample chamber, the magnetic particles of different reservoirs migrate predominantly to different sensitive zones. Thus a mixing of magnetic particles can be avoided.

20 Claims, 4 Drawing Sheets

(51) Int. Cl.
*B03C 1/28* (2006.01)
*G01N 27/74* (2006.01)
*G01N 33/94* (2006.01)

(52) U.S. Cl.
CPC ..... *G01N 27/745* (2013.01); *G01N 33/54373* (2013.01); *G01N 33/946* (2013.01); *G01N 33/948* (2013.01); *G01N 33/9486* (2013.01); *B03C 2201/18* (2013.01); *B03C 2201/26* (2013.01)

(56) References Cited

U.S. PATENT DOCUMENTS

| 2003/0190608 A1 | 10/2003 | Blackburn |
| 2004/0197845 A1 | 10/2004 | Hassibi |
| 2008/0009766 A1 | 1/2008 | Holmes |

FOREIGN PATENT DOCUMENTS

| WO | 9322678 A2 | 11/1993 |
| WO | 03062787 A2 | 7/2003 |
| WO | 03067258 A1 | 8/2003 |
| WO | 2005010542 A2 | 2/2005 |
| WO | 2005010543 A1 | 2/2005 |
| WO | 2006079998 A1 | 8/2006 |

OTHER PUBLICATIONS

Panhorst et al "Sensitive Bondforce Measurements of Ligand-receptor Pairs with Magnetic Beads" Biosensors and Bioelegronics, vol. 20, 2005, pp. 1685-1689.
Aytur et al "A Novel Magnetic Bead Bioassay Platform using a Microchip-based Sensor for Infectious Disease Diagnosis", Journal of Immunological Methods, vol. 314, 2006, pp. 21-29.

CARTRIDGE FOR ASSAYS WITH MAGNETIC PARTICLES

This application is a continuation of U.S. patent application Ser. No. 12/922,887, which is a national stage application under 35 U.S.C. § 371 of International Application No. PCT/IB2009/051021 filed on Mar. 11, 2009, which claims priority to European Application No. EP 08102671.8 filed on Mar. 17, 2008, the entire contents of each of which are incorporated herein by reference thereto.

The invention relates to a cartridge and a method for the detection of target components in a liquid sample with the help of magnetic particles, to a sensor device comprising such a cartridge, and to the use of such a cartridge and sensor device.

A magnetic sensor device is known from the WO 2005/010543 A1 and WO 2005/010542 A2 which may for example be used in a microfluidic biosensor for the detection of molecules, e.g. biological molecules, labeled with magnetic beads. The magnetic sensor device is provided with an array of sensor units comprising wires for the generation of a magnetic field and Giant Magneto Resistances (GMR) for the detection of stray fields generated by magnetized beads. The signal of the GMRs is then indicative of the number of the beads that are bound to an adjacent contact surface.

Based on this background it was an object of the present invention to provide means for the detection of target components in a sample with the help of magnetic particles, wherein it is desirable that a simultaneous detection of different target components is possible with a high accuracy.

A cartridge according to the present invention serves for the detection of target components in a liquid sample, for example of atoms, (bio-)molecules, complexes, drugs (especially drugs-of-abuse), nano-particles, micro-particles, cell fractions or cells in a body fluid like blood, saliva or urine. The detection of the target components may be qualitative (yielding only a present/not-present information) or preferably be quantitative (yielding e.g. the concentration of target components in the sample). The cartridge will typically be a low-cost plastic part made by injection molding, which can be filled with a sample to be tested, inserted into a corresponding reader for making the desired measurements, and thereafter be disposed. In general, the term "cartridge" shall however denote a device defined only by the following components:

a) A "sample chamber" which can be filled with the sample to be tested and in which a "magnetic actuation field" of a given configuration can be established. The sample chamber is typically an empty cavity; it may be an open cavity, a closed cavity, or a cavity connected to other cavities by fluid connection channels.

The configuration of the magnetic actuation field is described by the spatial course of its magnetic field lines and by the magnitude of the field (i.e. by the direction and length of the magnetic field vectors). For the definition of the cartridge, the configuration of the magnetic actuation field is considered as being predetermined and fixed relative to the cartridge.

The magnetic actuation field may be generated by internal means of the cartridge and/or by external means. The design of the cartridge shall in any case be such that the magnetic actuation field with the given configuration can be established in the sample chamber, i.e. the sample chamber may for example not be magnetically shielded. The magnetic actuation field can affect the migration of magnetic particles in the sample chamber by forces exerted on them e.g. via a nonzero field gradient. It should be noted that the magnitude of the magnetic field vectors will usually have to be above some threshold to make the magnetic influence strong enough (in competition to other influences, e.g. gravity).

b) At least two "reservoirs" for magnetic particles that are soluble in the sample. The magnetic particles may particularly comprise complexes, nano-particles, microparticles etc. that are magnetized or that can be magnetized in an external magnetic field; most preferably, they comprise superparamagnetic beads with a biocompatible coating on their surface.

Each reservoir may be a connected or a disconnected area/volume. The reservoirs may already be filled with magnetic particles or still be empty (i.e. only ready for taking up said particles).

c) At least two "sensitive zones" (regions) in which magnetic particles and/or target components can (qualitatively or quantitatively) be detected, for example if they enter these zones via a liquid sample in which they are solved. The sensitive zones may for example be located on a transparent wall of the sample chamber such that they can be optically accessed from the outside.

Moreover, the relation between the sample chamber, the reservoirs, the sensitive zones, and the given magnetic actuation field shall be such that magnetic particles of different reservoirs will predominantly reach different sensitive zones (if they reach a sensitive zone at all) when they migrate in a sample filling the sample chamber under the influence of the magnetic actuation field. As the movement of microscopic particles will always be subject to random influences, it suffices if the mentioned condition is "predominantly" satisfied, i.e. for more than 90% of the number of magnetic particles, preferably for more than 95%, most preferably for more than 99%.

The described cartridge allows a parallel testing of a sample with magnetic particles from different reservoirs and with different sensitive zones, wherein the magnetic particles can be affected by the magnetic actuation field (e.g. moved in a desired direction). Favorably, the effect of the magnetic actuation field on the magnetic particles is such that magnetic particles from different reservoirs do not mix during migration to the sensitive zones and during the interaction with the sensitive zones. The magnetic actuation field thus constitutes some kind of virtual walls (only) for the magnetic particles that effectively separate the sample chamber into distinct sub-chambers between which no exchange of magnetic particles takes place. Actually, the sample chamber remains however a connected volume in which the sample liquid can freely spread.

It should be noted that magnetic particles from one reservoir may migrate in a one-to-many relation to different sensitive zones, though there will typically be a one-to-one relation between reservoirs and sensitive zones.

In general, the configuration of the given magnetic actuation field may be quite arbitrary. In many cases, the field gradient, i.e. the gradient of the (scalar) amplitude of the magnetic field strength, will however be perpendicular to the sensitive zones (and optionally also to the reservoirs). More precisely, the sensitive zones may extend in a common plane, wherein the magnetic actuation field gradient crosses this plane substantially perpendicularly (i.e. under angles between about 70° and 110°, preferably between about 80° and 100°). As magnetic particles usually move in the direction of the magnetic field gradient, the described configuration will lead to a movement of particles perpendicularly to the sensitive zones (and reservoirs).

The reservoirs of the cartridge may for the use of the cartridge be filled with magnetic particles of identical type (material, size distribution, coating etc.). Preferably, at least two reservoirs are however filled with magnetic particles of different type, in particular with magnetic particles that are specific with respect to different target components. The magnetic particles of the two reservoirs may for example be coated with different molecules that (bio-)chemically bind to different target components in a sample and/or to different binding sites in the sensitive zones.

Similar remarks apply to the sensitive zones, i.e. at least two sensitive zones are preferably specific with respect to different target components. These zones may for example be coated with binding sites (capture molecules) that specifically bind to different target components in the sample. Thus it is possible to screen a sample in parallel for different target components.

The relative arrangement of reservoirs and sensitive zones is quite arbitrary as long as, in combination with a given magnetic actuation field, the desired separated movement of magnetic particles from reservoirs to sensitive zones is guaranteed. In a preferred embodiment, the reservoirs and the sensitive zones are located on different inner surfaces of the sample chamber, particularly on surfaces that face each other (e.g. the top and the bottom surface of the sample chamber). In this case the magnetic particles will have to migrate through the whole sample chamber to reach the sensitive zones, which maximizes the chances of a reaction between magnetic particles and target components in the sample.

In another embodiment, the reservoirs overlap (completely or at least partially) with the corresponding sensitive zones. In this case the magnetic particles are in the "right" sensitive zones already from the beginning of a measurement on, and the magnetic actuation field has only to guarantee that they do not leave the sphere of this sensitive zone and reach another sensitive zone.

According to still another embodiment, the reservoirs are disposed on the same surface as the sensitive zones and next to their corresponding sensitive zones. The arrangement of reservoirs and sensitive zones on a common surface facilitates the manufacture of the cartridge as only one surface has to be processed.

When magnetic particles move from different reservoirs to the corresponding sensitive zones, they may mutually interact for example by magnetic and/or electrostatic forces. To avoid undesirable effects of such an interaction on the migration of the magnetic particles, it is preferred that the reservoirs are filled with amounts of magnetic particles that substantially balance mutual interactions between magnetic particles of different reservoirs during their migration through the sample. In a symmetric arrangement of two reservoirs and two sensitive zones, equal amounts of magnetic particles in both reservoirs may for example be applied to make mutual interactions between the magnetic particles symmetrical, too.

The sample chamber is preferably a part of a fluidic system or connected to a fluidic system by which a sample flow can be induced through the sample chamber. This allows to fill the sample chamber with a liquid sample when a measurement shall be made.

In the most simple case, the cartridge may be a device (e.g. a molded plastic part) that substantially only consists of the sample chamber with regions serving as reservoirs and other regions serving as sensitive zones. In a more sophisticated embodiment, the cartridge comprises an integrated magnetic field generator, for example a coil and/or a wire embedded into the walls of the cartridge through which electrical currents can be led for inducing a magnetic field. The magnetic field generator may particularly be adapted to generate the magnetic actuation field that influences the migration of the magnetic particles from the reservoirs to the sensitive zones. The magnetic field generator may however also or alternatively serve other purposes, for example the magnetic excitation of magnetic particles in the sensitive zones to generate stray fields that give away the presence of these particles to a suitable magnetic sensor.

According to another embodiment, the cartridge may comprise an integrated sensor unit for detecting magnetic particles and/or target components in the sensitive zones. Integrating such a sensor unit into the cartridge has the advantage to minimize the distance between sensor and sample and to guarantee definite operating conditions.

The invention further relates to a sensor device for the detection of target components in a liquid sample, comprising the following components:
 a) A cartridge of the kind described above, i.e. a cartridge with a sample chamber and at least two reservoirs and sensitive zones, wherein magnetic particles of different reservoirs will reach different sensitive zones when migrating under the influence of a given magnetic actuation field.
 b) A magnetic field generator for generating the magnetic actuation field inside the cartridge. The magnetic field generator may for example be realized by a permanent magnet or an electromagnetic coil, and it may the integrated into the cartridge or external to it.
 c) A sensor unit for detecting magnetic particles and/or target components inside the cartridge. Again, the sensor unit may (at least partially) be integrated into the cartridge or be a separate component of the sensor device.

As the cartridge is an important component of the sensor device, reference is made to the above description of said cartridge for more information on details, advantages and further developments of the sensor device.

The cartridge and/or the sensor device may optionally comprise an optical, magnetic, mechanical, acoustic, thermal and/or electrical sensor unit. A magnetic sensor unit may particularly comprise a coil, Hall sensor, planar Hall sensor, flux gate sensor, SQUID (Superconducting Quantum Interference Device), magnetic resonance sensor, magneto-restrictive sensor, or magneto-resistive sensor of the kind described in the WO 2005/010543 A1 or WO 2005/010542 A2, especially a GMR (Giant Magneto Resistance), a TMR (Tunnel Magneto Resistance), or an AMR (Anisotropic Magneto Resistance). An optical sensor unit may particularly be adapted to detect variations in an output light beam that arise from a frustrated total internal reflection due to target particles at a sensing surface. Other optical, mechanical, acoustic, and thermal sensor concepts are described in the WO 93/22678, which is incorporated into the present text by reference.

Moreover, the invention relates to a method for the detection of target components in a liquid sample which comprises the following steps (wherein the sequence of their enumeration does not necessarily correspond to their temporal order):
 Filling the sample chamber of a cartridge with the sample. The cartridge may particularly be one of the kind described above.

Letting magnetic particles migrate through the sample from at least two reservoirs to at least two sensitive zones. In this context, the term "letting" shall mean that conditions are provided under which magnetic particles can migrate through the sample. Such conditions may comprise for example enough time, appropriate temperature, initial provision of enough magnetic particles in the reservoirs, dissolution of the magnetic particles in the sample etc.

Establishing a magnetic actuation field of a given configuration in the sample chamber such that magnetic particles of different reservoirs will predominantly migrate to different sensitive zones. The magnetic actuation field may optionally be present throughout the whole procedure.

Detecting magnetic particles and/or target components in the sensitive zones.

The method comprises in general form the steps that can be executed with a cartridge and a sensor device of the kind described above. Therefore, reference is made to the preceding description for more information on the details, advantages and improvements of that method.

The invention further relates to the use of the cartridge and/or the sensor device described above for molecular diagnostics, biological sample analysis, or chemical sample analysis, food analysis, and/or forensic analysis. Molecular diagnostics may for example be accomplished with the help of magnetic beads or fluorescent particles that are directly or indirectly attached to target molecules.

These and other aspects of the invention will be apparent from and elucidated with reference to the embodiment(s) described hereinafter. These embodiments will be described by way of example with the help of the accompanying drawings in which.

Like reference numbers or numbers differing by integer multiples of 100 refer in the Figures to identical or similar components.

Figure 1:
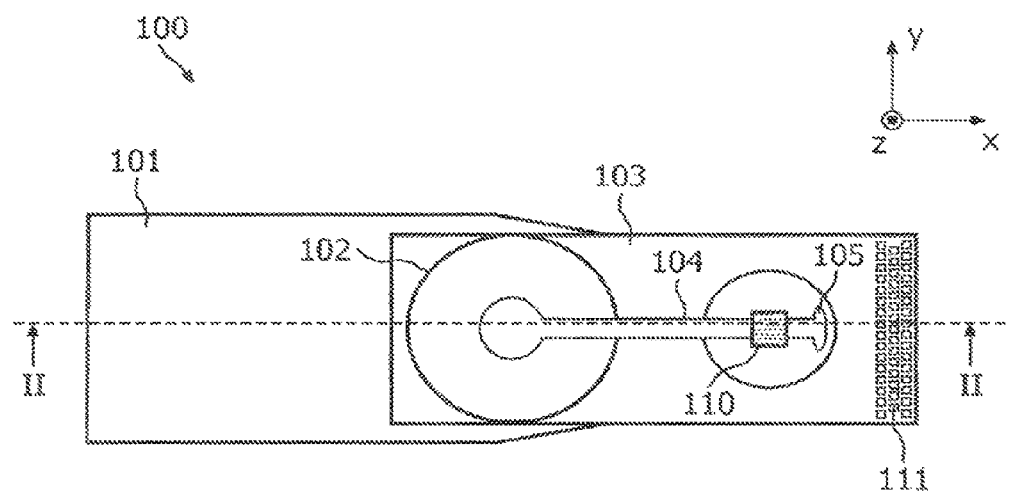
FIG. 1 shows a top view onto a first cartridge according to the present invention in which particle reservoirs and sensitive zones are located on a top part and a bottom part, respectively.

A roadside drugs-of-abuse test is a typical application of a portable magnetic biosensor. Such a test will be used in traffic (similar to a breath alcohol test), and must be able to verify the presence of up to five drugs in a single saliva sample within one minute. The test should be reliable and easy to use. Preferably it should be done with only one operator action (taking the sample and inserting it into a reader) without any training of the police force.

An illicit drug is in general a small molecule that is capable of binding only one capture molecule (antibody). For this reason an inhibition or competition assay format may be used for the detection of such drugs. In an assay of a first type target homologue molecules are present on a sensor surface. These target homologue molecules compete with the target component (that might be present in the sample) for binding to a capture molecule that is present on a magnetic label. In a second type of assay the target homologue is present on the magnetic label and the coated label competes with the target component (that might be present in the sample) for binding to capture molecules (antibodies) that are present on a sensor surface.

In the aforementioned exemplary scenarios, five different capture molecules need to be present on the magnetic label or on the sensor surface (depending on the assay format) to be able to detect five drugs. Furthermore, five different target homologues need to be present on the sensor surface or on the magnetic label (depending on the assay format). Because the drug is generally a small molecule, the binding to other molecules via a receptor-ligand binding (e.g. binding to an antibody) is generally not very specific. As a result, cross-reaction occurs (e.g. a magnetic label coated with binding molecules for type A binds to a target homologue of type B). For example magnetic particles coated with anti-amphetamine antibodies will bind to BSA-amphetamine conjugates on the sensor surface, but will also bind significantly to BSA-methamphetamine. So adding magnetic particles with anti-amphetamine antibodies to an array of sensitive zones with at least one sensitive zone coated with BSA-amphetamine and one sensitive zone coated with BSA-methamphetamine will show a large sensor output for the sensitive zone coated with BSA-amphetamine, but will also show a significant output signal for the sensitive zone coated with BSA-methamphetamine. Therefore, in most test systems the assays showing cross-reaction are physically separated by performing the assays in separate test strips/tubes. This is a complex solution, since the test sample needs to be divided over the different test strips/tubes, leading to a complex test device and an increased sample volume needed to perform all tests.

The solution to the above problems that is proposed here relies on the fact that in a magnetic biosensor one can make use of the actuation possibilities that are offered by the magnetic labels (beads). To this end, the orientation of the magnetic forces and the relative position of the magnetic particles are chosen such that different types of particles do not mix.

FIGS. 1 to 4 show a cartridge 100 according to a first realization of the aforementioned principles. The cartridge 100 comprises the following components:

A top part 101, for example produced as an injection molded plastic part. The top part 101 comprises a funnel-shaped sample inlet 102 on its upper side which leads into a fluidic channel 104. This channel 104 is engraved into the bottom side and ends in a liquid stop and venting hole 105. Moreover, the top part 101 comprises two neighboring reservoirs 131, 132 that are filled with (different) magnetic particles MP, MP'.

A bottom part 103 that is attached to the upper part 101 and for example realized as a molded interconnection device (MID). The bottom part 103 comprises a conical through hole that establishes a sample chamber SC below the reservoirs 131, 132.

A sensor unit 110 that is attached to the bottom side of the bottom part 103 to close the sample chamber SC. The sensor unit 110 comprises means for the detection of target components and/or magnetic particles in sensitive zones 121, 122 on its surface. The sensor unit 110 may for example simply be a transparent body through which an input light beam L1 from a light source (not shown) can be directed to the interface between this body and the sample chamber SC, where it is totally internally reflected into an output light beam L2. Target components and/or magnetic particles that are bound at the interface will then lead to a frustrated total internal reflection (FTIR), which can be detected in the output light beam L2 with the help of a light detector (not shown).

Alternatively, the sensor unit might also comprise a magneto-restrictive sensor like a GMR sensor.

The sensor unit 110 can electrically be contacted by a reader (not shown) via contact pads 111 on an electrical flex foil (MID).

Figure 2:
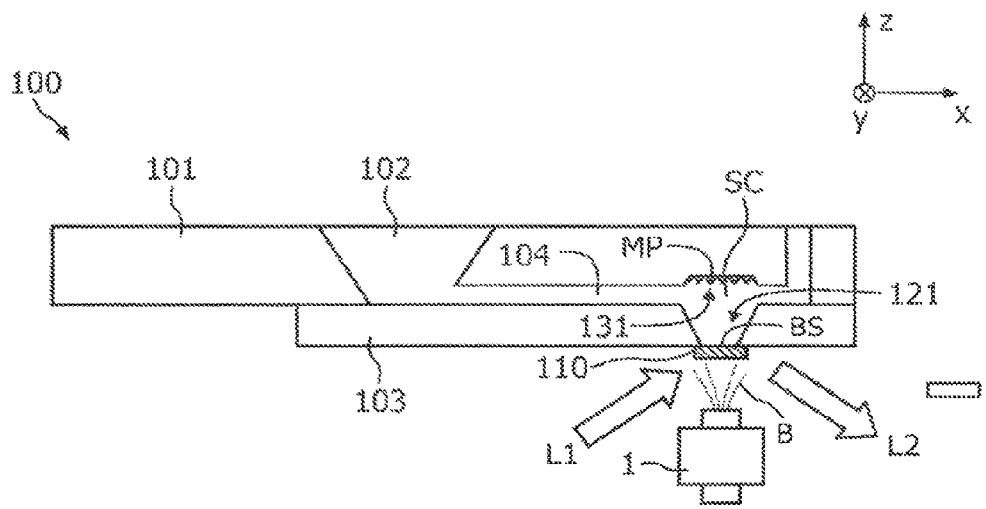
FIG. 2 shows a section through the first cartridge along line II-II of FIG. 1.
Figure 3:
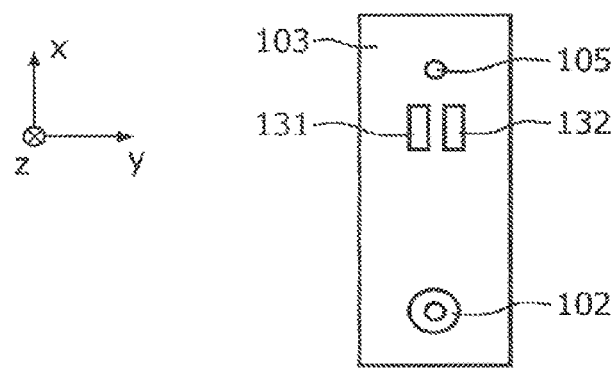
FIG. 3 shows a bottom view onto the top part of the first cartridge.

Moreover, FIG. 2 shows a magnetic field generator 1 disposed below the sensor unit 110 for generating a magnetic actuation field B with a predetermined configuration inside the sample chamber SC.

Figure 4:
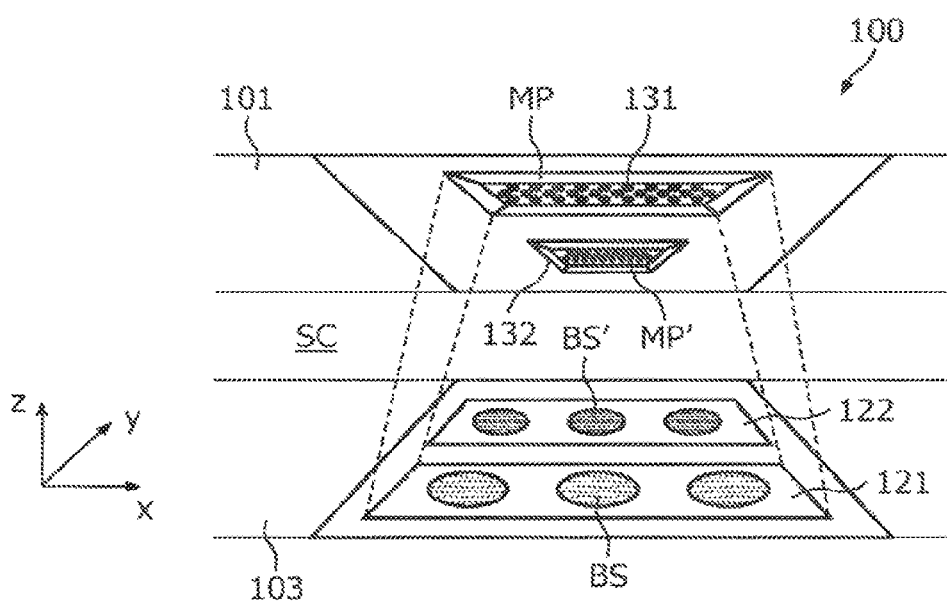
FIG. 4 shows a perspective view into the sample chamber of the first cartridge.

FIG. 4 illustrates in a perspective view into the sample chamber SC the relative arrangement of two reservoirs 131, 132 on the roof of the sample chamber and corresponding two sensitive zones 121, 122 on the bottom of the sample chamber. The sensitive zones 121 and 122 each comprise a plurality of binding spots BS and BS', respectively. The binding spots BS or BS' within each sensitive zone are coated with the same capture molecules, while the binding spots BS and BS' of different sensitive zones are coated with different capture molecules. The capture molecules can for example be deposited in small spots by means of inkjet printing.

The two reservoirs 131 and 132 are furnished with magnetic particles MP, MP' of different type, i.e. specific to different target components in the sample (e.g. in saliva) filling the sample chamber SC. The magnetic particles may initially be present in a dried form (e.g. a sugar matrix). The sample fluid will dissolve the dry matrix. Magnetic actuation can then be switched on to transport the magnetic particles (in negative z-direction) towards the sensor surface where they are able to bind specifically. As illustrated in FIG. 4 by dashed lines for one reservoir, the magnetic particles of the reservoirs 131 and 132 will migrate under the influence of the (gradient of the) magnetic actuation field B predominantly to just the corresponding sensitive zone 121 and 122, respectively, below them. An advantage of such a migration through the whole sample chamber SC is that the beads come into contact with the full sample volume, which causes the assay to be highly sensitive.

In FIG. 4, the main magnetic force component is directed in (negative) z-direction, i.e. perpendicular to the sensor surface, and the magnetic beads MP, MP' in the reservoirs are located in z-direction exactly above their corresponding capture sites on the sensor surface. The in plane components (in x and y direction) are much smaller. The magnetic field lines may preferably be oriented along the x-direction (with their gradient pointing in z-direction), which creates strings of magnetic particles along these field lines. This creates a repulsive force between the strings of magnetic particles in the y-direction, which aids in keeping the two populations of beads separated.

When the center of the magnet 1 that generates the field is well aligned with the center of the binding surface, the magnetic beads do not cross the center (stable magnetic point), which prevents mixing of the beads by magnetic means. Mixing by diffusion can be neglected since the magnetic forces can be made sufficiently high. As magnetic beads can however cross the center of the magnet by repulsive electrostatic and/or magnetic forces between the magnetic particles and chains of particles, respectively, both reservoirs are preferably filled with approximately equal numbers of magnetic beads to form a sort of "counter pressure".

It should be noted that magnetic excitation fields, which may be used to magnetize the beads during a detection procedure with a GMR sensor in the sensitive zones are typically very localized and do not cause undesired mixing of the beads.

It should further be noted that of course more than two types of beads can be deposited in reservoirs next to each other, depending on the space available. With this method, multiple assays that would cross-react with each other if they are mixed can be performed in the same reaction chamber, without having any cross-reactions.

Figure 5:
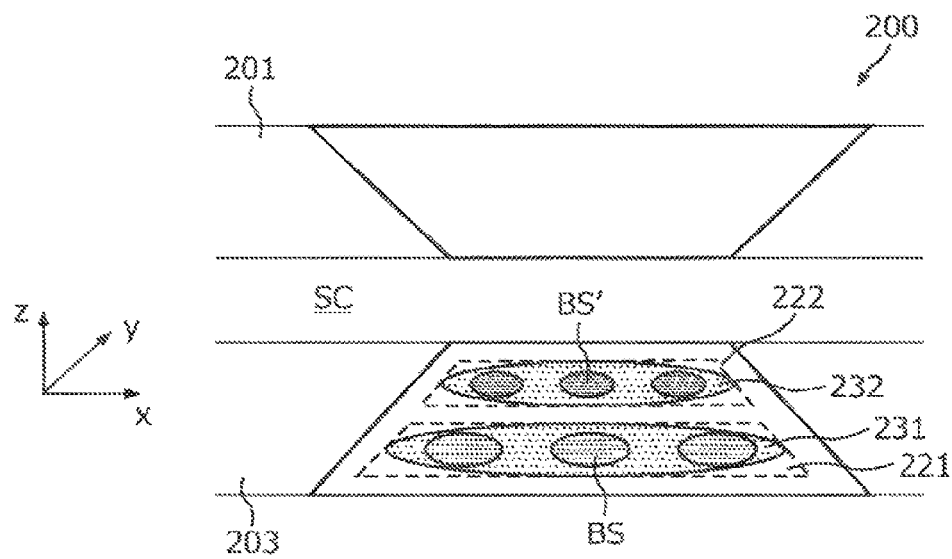
FIG. 5 shows a perspective view into the sample chamber of a second cartridge according to the present invention in which particle reservoirs and sensitive zones overlap.

FIG. 5 illustrates a second embodiment of a cartridge 200. Different magnetic beads coated with different binding molecules or different target homologues are applied to separate reservoirs 231 and 232, respectively, which are located directly on the same surface as and overlap with the sensitive zones 221 and 222. An advantage of this design is that all biomaterial is put on one part of the cartridge (in FIG. 5 the bottom part 203 containing the bottom of the sample chamber SC). This part can therefore be optimized for applying biomaterials, while the other part (201) can be optimized for e.g. ensuring quick filling of the fluidic channels. Such an optimization may for instance comprise a hydrophilization (which would make the application of biomaterial in small spots very difficult). Another advantage is that the magnetic beads are already very close to the sensor surface and do not need time to move from the top part down to the sensor surface, thus decreasing the assay time.

Figure 6:
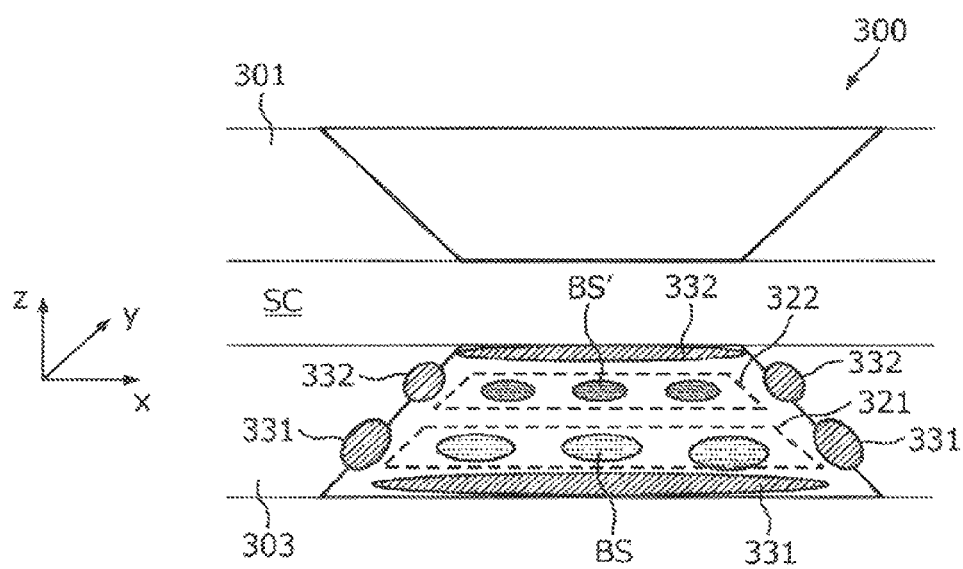
FIG. 6 shows a perspective view into the sample chamber of a third cartridge according to the present invention in which the particle reservoirs surround the sensitive zones.

FIG. 6 illustrates a third embodiment of a cartridge 300. Again, the bead reservoirs 331 and 332 are located on the bottom of the sample chamber SC, i.e. on the bottom part 303. However, instead of depositing the beads on top of the printed binding spots BS, BS', i.e. in overlap with the sensitive zones 321 and 322, they are deposited next to the printed binding spots. The beads can be deposited next to the binding spots in the x- and/or y-direction. The binding spots can also be printed in a circular layout, the corresponding beads can then be deposited next to their corresponding capture site, in a somewhat bigger circle or ring surrounding them.

Figure 7:
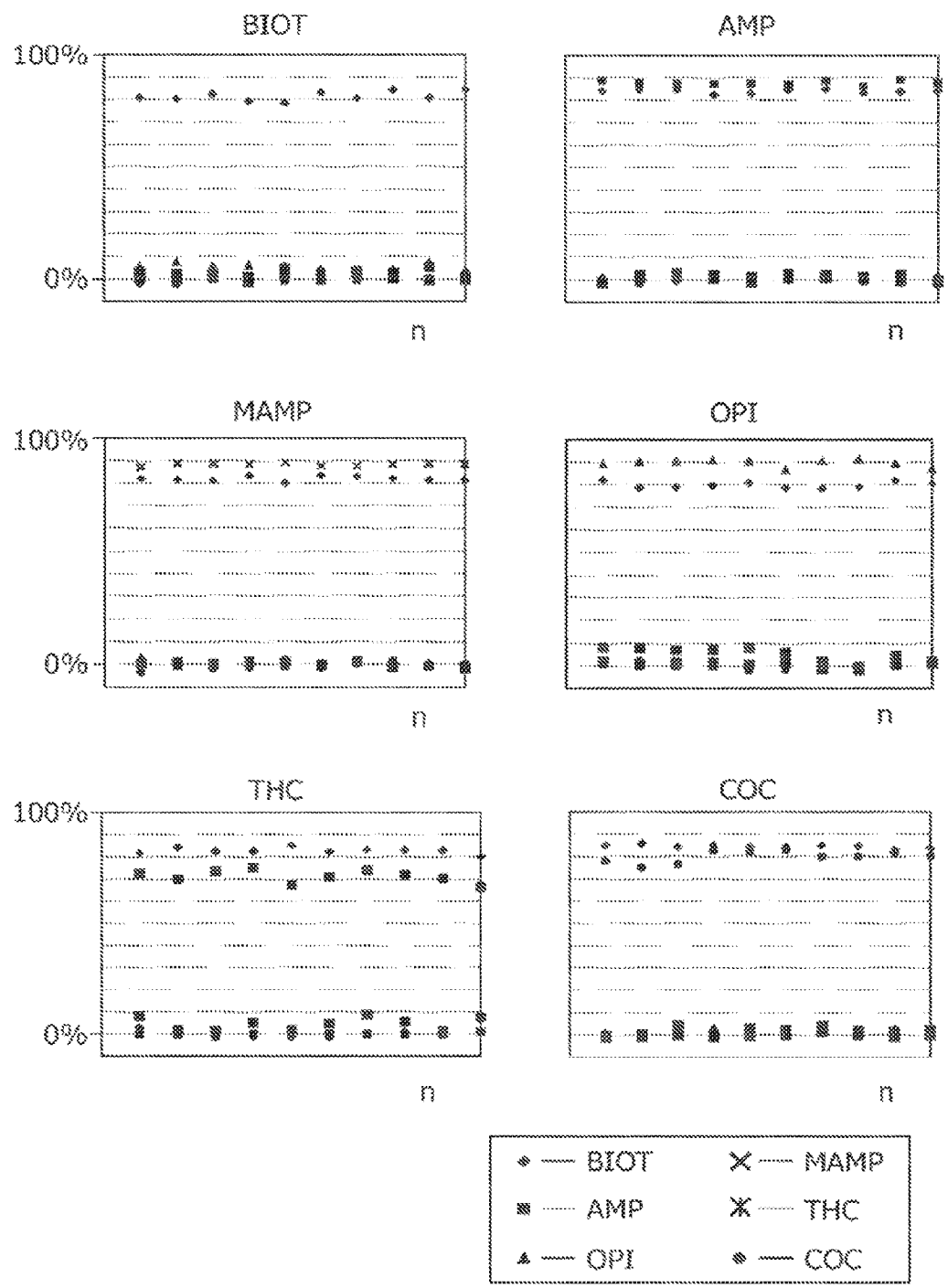
FIG. 7 shows various diagrams of an experimental test of a cartridge and method according to the invention.

FIG. 7 summarizes results of an experiment that shows the feasibility of the magnetic separation with two different reservoirs (wells). In the experiment, a competitive assay was performed on an optical FTIR sensor system. Five drugs (opiates OPI, amphetamine AMP, metamphetamine MAMP, cocaine COC, tetrahydrocannabinol THC) and a reference (biotin BIOT) were measured simultaneously. The total assay time was one minute. Magnetic particles were present in dry form, the reagents were neat, filtered saliva (dry reagents).

Superparamagnetic particles were coated with monoclonal anti-drug antibodies. For the amphetamine, biotin and opiate assay, Ademtech 500 nm COOH coated particles were used. For metamphetamine, cocaine and tetrahydrocannabinol assay, Ademtech 300 nm $NH_2$ beads were used. The particles were redispersed in a drying buffer. The 500 nm beads were redispersed at 1 wt % each (total bead concentration 3 wt %, mixture 1) whereas the 300 nm beads were redispersed at 2 wt % (COC and THC) or 1 wt % (total bead concentration 5%, mixture 2). Subsequently, 2×75 nl of mixture 1 and mixture 2 were deposited on a fluidic top part containing two wells, one mixture in each well. The optical substrate was prepared for detection of the target molecules by printing spots of BSA-drug. The top and bottom part of the biosensor was assembled by using tape, and the sensors were kept under lab conditions at room temperature. Next day, the cartridges were tested by performing a competitive assay in the optical biosensor system. The assay comprised filtering saliva (pool of 10 volunteers) over a stack of filter-hydroxy apatite (HAP)-filter, whereby the filters contain the dry reagents. Next, the filtered saliva was spiked with different concentrations of drugs and inserted in the cartridge by autonomous filling through a capillary channel. Next, the magnetic particles redispersed and were subsequently attracted to the sensor surface (using an actuation coil system). After a predetermined time, the magnetic attraction field was removed. Another magnetic field above the cartridge was applied to pull the non-bound beads away from the substrate surface. The total assay time (filling, redispersion and magnetic actuation) was 60 s (1 s cartridge filling, 14 s beads redispersion, 45 s actuation.). The cross reactivity was then measured.

With ten negative samples (all drugs negative) and ten positive samples per drug (i.e. one drug negative, rest strongly positive) and biotin the cross-talk was measured. Positive concentration was chosen at 1 µg/ml (for opiates, amphetamine, metamphetamine, biotin), 5 µg/ml (for cocaine) and 50 µg/ml (for tetrahydrocannabinol). FIG. 7 shows in six diagrams the optical signal change of the spots on the optical substrates (in %) for saliva mixtures containing all drugs but one that is indicated in the header of the diagrams (i.e. no biotin BIOT, no amphetamine AMP, no opiates OPI, no metamphetamine MAMP, no THC, and no cocaine COC; horizontal axis: number of measurement).

All drug-positive spots have signal changes below 10%, thereby showing a very low cross-talk. Further, magnetic particles coated with anti-amphetamine antibodies do not bind to BSA-methamphetamine. If the separation between the two rows would not be good, the BSA-Metamphetamine spots would show similar signals to the signals from the BSA-Amphetamine spots, thereby showing prefect separation between the Amphetamine-Metamphetamine assays.

In summary, a solution was presented to keep magnetic beads separated during the binding process. By depositing magnetic beads in at least two different reservoirs that are oriented perpendicular to the direction of the magnetic field lines, the groups of beads will not show any mixing during the assay. This allows performing multiple assays in a single chamber without any problems with cross-reactivity.

Advantages of this approach are inter alia:
no cross-reactivity;
low cartridge complexity: one channel, one chamber;
small sample volume required: sample does not need to be split.

While the invention was described above with reference to particular embodiments, various modifications and extensions are possible, for example:

The sensor can be any suitable sensor to detect the presence of magnetic particles on or near to a sensor surface, based on any property of the particles, e.g. it can detect via magnetic methods (e.g. magnetoresistive, Hall, coils), optical methods (e.g. imaging, fluorescence, chemiluminescence, absorption, scattering, evanescent field techniques, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), combinations thereof, etc.

The magnetic sensor can be any suitable sensor based on the detection of the magnetic properties of the particle on or near to a sensor surface, e.g. a coil, magneto-resistive sensor, magneto-restrictive sensor, Hall sensor, planar Hall sensor, flux gate sensor, SQUID, magnetic resonance sensor, etc.

Molecular targets often determine the concentration and/or presence of larger moieties, e.g. cells, viruses, or fractions of cells or viruses, tissue extract, etc.

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

Measurement data can be derived as an end-point measurement, as well as by recording signals kinetically or intermittently.

The particles serving as labels can be detected directly by the sensing method. As well, the particles can be further processed prior to detection. An example of further processing is that materials are added or that the (bio)chemical or physical properties of the label are modified to facilitate detection.

The device and method can be used with several biochemical assay types, e.g. binding/unbinding assay, sandwich assay, competition assay, displacement assay, enzymatic assay, etc. It is especially suitable for DNA detection because large scale multiplexing is easily possible and different oligos can be spotted via ink-jet printing on a substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

With nano-particles are meant particles having at least one dimension ranging between 3 nm and 5000 nm, preferably between 10 nm and 3000 nm, more preferred between 50 nm and 1000 nm.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A cartridge for the detection of target components in a liquid sample, comprising:
magnetic particles;
a sample chamber configured to receive the liquid sample devoid of the magnetic particles and in which a magnetic actuation field of a given configuration can be established;
at least two reservoirs that are located in the sample chamber and store the magnetic particles, wherein the stored magnetic particles are configured to be released in the liquid sample in response to filling the sample chamber with the liquid sample under influence of the magnetic actuation field;
at least two sensitive zones in which at least one of the magnetic particles and target components can be detected,
wherein a first reservoir of the at least two reservoirs includes first magnetic particles which are different from magnetic particles of other reservoirs of the at least two reservoirs, the first reservoir being associated with a first sensitive zone of the at least two sensitive zones so that the first magnetic particles when migrating in the liquid sample filling the sample chamber from the first reservoir, under influence of the magnetic actuation field, will predominantly reach the first sensitive zone without predominantly reaching another sensitive zone of the at least two sensitive zones associated with another reservoir of the at least two reservoirs, and
wherein the at least two reservoirs are disposed on a same surface as the at least two sensitive zones.

2. The cartridge according to claim 1, wherein the sensitive zones extend in a common plane and that a gradient in the magnetic actuation field crosses this plane substantially perpendicularly.

3. The cartridge according to claim 1, wherein the at least two reservoirs are filled with magnetic particles that are specific with respect to different target components.

4. The cartridge according to claim 1, wherein the at least two sensitive zones are specific with respect to different target components.

5. The cartridge according to claim 1, wherein the at least two reservoirs overlap with the corresponding sensitive zones.

6. The cartridge according to claim 1, wherein the at least two reservoirs are next to the at least two sensitive zones.

7. The cartridge according to claim 1, wherein the at least two reservoirs are filled with amounts of the magnetic particles that substantially balance mutual interactions when the magnetic particles migrate in the liquid sample.

8. The cartridge according to claim 1, wherein the sample chamber is part of or connected to a fluidic system via which a sample flow can be directed through the sample chamber.

9. The cartridge according to claim 1, further comprising an integrated magnetic field generator.

10. The cartridge of claim 9, wherein the integrated magnetic field generator comprises at least one of a coil and a wire embedded into walls of the cartridge through which electrical currents can be led for inducing the magnetic actuation field.

11. The cartridge according to claim 1, further comprising an integrated sensor unit for detecting at least one of the magnetic particles and target components in the at least two sensitive zones.

12. The cartridge according to claim 1, further comprising at least one optical, magnetic, mechanical, acoustic, thermal or electrical sensor unit, including a coil, a Hall sensor, a planar Hall sensor, a flux gate sensor, a SQUID, a magnetic resonance sensor, a magneto-restrictive sensor, or magneto-resistive sensor like a GMR, a TMR, or an AMR element.

13. The cartridge of claim 1, further comprising a magnetic field generator for generating the magnetic actuation field, wherein a center of the magnetic field generator is aligned with a center of a binding surface of the sample chamber including the at least two sensitive zones.

14. The cartridge of claim 1, wherein the at least two reservoirs are configured to hold equal numbers of the magnetic particles.

15. The cartridge of claim 1, further comprising at least one optical sensor unit having a transparent body for passage of input light into the sample chamber for total internal reflection, and for passage of output light from the sample chamber resulting from a frustrated total internal reflection resulting from magnetic particles that are bound at an interface between the transparent body and the sample chamber.

16. The cartridge of claim 1, wherein the magnetic particles are stored in the at least two reservoirs located in the sample chamber in dry form.

17. A sensor device for the detection of target components in a liquid sample, comprising:
a cartridge comprising magnetic particles, a sample chamber which can be filled with the liquid sample devoid of the magnetic particles and in which a magnetic actuation field of a given configuration can be established, at least two reservoirs that are located in the sample chamber and store the magnetic particles, wherein the stored magnetic particles are configured to be released in the liquid sample in response to filling the sample chamber with the liquid sample under influence of the magnetic actuation field, and at least two sensitive zones in which at least one of the magnetic particles and target components can be detected;
a magnetic field generator for generating the magnetic actuation field inside the cartridge;
a sensor unit for detecting at least one of the magnetic particles and the target components inside the cartridge,
wherein a first reservoir of the at least two reservoirs includes first magnetic particles which are different from magnetic particles of other reservoirs of the at least two reservoirs, the first reservoir being associated with a first sensitive zone of the at least two sensitive zones so that the first magnetic particles when migrating in the liquid sample filling the sample chamber from the first reservoir, under influence of the magnetic actuation field, will predominantly reach the first sensitive zone without predominantly reaching another sensitive zone of the at least two sensitive zones associated with another reservoir of the at least two reservoirs, and
wherein the at least two reservoirs are disposed on a same surface as the at least two sensitive zones.

18. The sensor device of claim 17, wherein the magnetic field generator comprises at least one of a coil and a wire embedded into walls of the cartridge through which electrical currents can be led for inducing the magnetic actuation field.

19. The sensor device of claim 17, wherein the at least two reservoirs are configured to hold equal numbers of the magnetic particles.

20. The sensor device of claim 17, wherein the magnetic particles are stored in the at least two reservoirs located in the sample chamber in dry form.

* * * * *